US000001347H

United States Statutory Invention Registration [19]

[11] Reg. Number: H1347

[43] Published: Aug. 2, 1994

Greeninger et al.

[54] AUDIO FEEDBACK FOR IMPLANTABLE MEDICAL DEVICE INSTRUMENTS

[75] Inventors: Daniel R. Greeninger, Coon Rapids; David L. Thompson, Fridley, both of Minn.

[73] Assignee: Medtronic Inc., Minneapolis, Minn.

[21] Appl. No.: 973,358

[22] Filed: Nov. 9, 1992

[51] Int. Cl.[5] ..... A61N 1/36

[52] U.S. Cl. ..... 607/30; 607/60

[58] Field of Search ..... 128/903, 653.5; 607/30, 607/32, 60

[56] References Cited

U.S. PATENT DOCUMENTS

| | | | |
|---|---|---|---|
| 4,236,524 | 12/1980 | Powell et al. | 128/419 |
| 4,250,884 | 2/1981 | Hartlaub | 128/419 |
| 4,305,397 | 12/1981 | Weisbrod | 128/419 |
| 4,323,074 | 4/1982 | Nelms | 128/419 |
| 4,432,360 | 2/1984 | Mumford | 128/419 |
| 4,832,033 | 5/1989 | Maher et al. | 128/421 |

*Primary Examiner*—David Brown

*Attorney, Agent, or Firm*—Reed A. Duthler; Harold R. Patton

[57] ABSTRACT

A method and apparatus for interpreting and displaying the status and diagnostic data of, and/or programming an implantable medical device is disclosed. The apparatus includes a microprocessor with multiple executable programs; data entry means, such as a keyboard or light pen; a display means such as a screen display and/or a printer; and may include a receiver and transmitter means for remote programming and interrogation of the implantable medical device. The apparatus further includes a stored audio signal to represent the status and diagnostic values of the implantable medical device.

22 Claims, 3 Drawing Sheets

A statutory invention registration is not a patent. It has the defensive attributes of a patent but does not have the enforceable attributes of a patent. No article or advertisement or the like may use the term patent, or any term suggestive of a patent, when referring to a statutory invention registration. For more specific information on the rights associated with a statutory invention registration see 35 U.S.C. 157.

AUDIO FEEDBACK FOR IMPLANTABLE MEDICAL DEVICE INSTRUMENTS

FIELD OF THE INVENTION

The invention relates generally to the field of programmable biomedical implantable devices and more particularly to audio feedback in external equipment such as programmers and analyzers used in conjunction with cardiac pacemakers, neurostimulators and the like.

BACKGROUND OF THE INVENTION

A wide variety of cardiac pacemakers are known and commercially available. Pacemakers are generally characterized by which chambers of the heart they are capable of sensing, the chambers to which they deliver pacing stimuli, and their responses, if any, to sense intrinsic electrical cardiac activity. Some pacemakers deliver pacing stimuli at fixed, regular intervals without regard to naturally occurring cardiac activity. More commonly, however, pacemakers sense electrical cardiac activity in one or both of the chambers of the heart, and inhibit or trigger delivery of pacing stimuli to the heart based on the occurrence and recognition of sensed intrinsic electrical events. A so called "VVI" pacemaker, for example, senses electrical cardiac activity in the ventricle of the patient's heart, and delivers pacing stimuli to the ventricle only in the absence of electrical signals indicative of natural ventricular contractions. A "DDD" pacemaker, on the other hand, senses electrical signals in both the atrium and ventricles of the patient's heart, and delivers atrial pacing stimuli in the absence of signals indicative of natural atrial contractions, and ventricular pacing stimuli in the absence of signals indicative of natural ventricular contractions. The delivery of each pacing stimulus by a DDD pacemaker is synchronized with prior sensed or paced events.

Pacemakers are also known which respond to other types of physiological based signals, such as signals from sensors for measuring the pressure inside the patient's ventricle or measuring the level of patient's physical activity. These labelled "VVIR" for a single chamber version or "DDDR" for a dual chamber version.

The complexity of modern pacemakers, the need to diagnose, optimize and adjust various parameters during the implant procedure, the occurrence of rare device failures, or more commonly, physiologic changes, and device variables or drift, dictate the need for numerous programmable parameters accessible non-invasively via an externally operated programmer. The need to assess system performance or troubleshoot the patient, device and/or lead system in an acute, clinical setting requires extensive telemetry capability in the implanted device and external programmer.

Modern programmers used to adjust the parameters of multi-function implantable medical devices, typically have graphic displays, keyboards or light pens for data entry and device control by operator manipulation, and printers or plotters to allow the user to easily control, evaluate and document the extensive capabilities of modern medical devices. An example of one such device is the Medtronic Model 9760 programmer. Typically, in use during an implant procedure in the surgical suite, the programmer is positioned outside the sterile field remote from the patient. A programming head, or wand containing transmitter and receiver circuitry, is connected to the programmer via a stretchable coiled cable, and positioned over the patient's pacemaker implant site for programing or telemetry interrogation of the implanted device. The programmer typically consists of 1 or more microprocessors and contains programmable memory capable of storing executable programs under the control of the operator via keyboard or light per entry. The physician in the sterile field verbally communicates programming directions to a nurse or associate at the control of programmer outside of the sterile field. The implanting physician often cannot see the screen or display on the programmer because of the distance involved, small size of the screen, or display screen contrast limitations. This requires the program operator to verbally communicate patient status, device function and status, and success or failure of requested program operations to the physician.

Similarly, during an implant, a Pacing Systems Analyzer (PSA) is typically used to verify cardiac pulse generator function and evaluate lead pacing threshold and intrinsic signal amplitude values. These values are utilized to set the programmable parameters of the implantable pulse generator to ensure an adequate safety margin for pacing and sensing, respectively. In use, the PSA is connected by test cables to the externalized proximal end of the lead system implanted in the patient. The PSA is held and controlled by an assistant who reports stimulation thresholds and R-wave/P-wave amplitudes on a beat-by-beat basis. The PSA typically contains pacing and sensing circuitry, under control of one or more microprocessors, and programmable memory capable of storing executable programs under the control of the operator via keyboard entry. This process is error prone due to the potential errors in the viewing of values on a small liquid crystal display (LCD) on a typical PSA and the verbal communication required to report to the attending physician.

In prior art, as the programmer operator enters strings of keystrokes to control the operation of the programmer, to set up programmable parameter values for the implanted device or to program or interrogate the implanted device, programmers have used an audio tone or "beep," either intermittently or steady, to confirm programmer and/or implanted device function and status. Examples of prior art audio feedback include U.S. Pat. No. 4,236,524 to R. Powell, et al., "Program Testing Apparatus"; U.S. Pat. No. 4,250,884 to J. Hartlaub, et al., "Apparatus For and Method of Programming the Minimum Energy Threshold For Pacing Pulses to be Applied to a Patient's Heart"; U.S. Pat. No. 4,305,397 to S. Weisbrod, et al., "Pacing Generator Programmer With Transmission Checking Circuit"; and U.S. Pat. No. 4,323,074 to G. Nelms "Pacemaker Programming Apparatus Utilizing a Computer System with Simplified Data Input"; all assigned to the assignee of the present invention and incorporated herein in their entirety by reference. All operate, or sound, a beeper for valid keystroke entries. The '884 and '397 patents also describe sounding a beeper to indicate programmer status such as a valid downlink programming or the completion of a timeout function. The '074 patent also describes sounding a beeper to indicate a successful battery check operation upon device turn-on. Additionally, U.S. Pat. No. 4,432,360 to U. Mumford, et al., "Interactive Programmer for Biomedical Implantable Devices" describes intermittently sounding a beeper upon power-up/self-test and at specific device function/status such as programming "STAT SET" or standard values. Additionally, a steady tone is sounded at the transmission of programming pulses and a pulsating tone at the end of transmission or during self-test failure. With the previously listed needs and shortcomings of prior art programmers and analyzers, the use of intermittent or steady tones is inadequate to meet complex present day requirements for patient safety and communication.

These and other problems are solved by the apparatus of this invention.

SUMMARY OF INVENTION

In accordance with this invention, there is provided audible spoken feedback and data to the user of various instruments such as programmers and pacing systems analyzers for implantable medical devices such as pacemakers, defibrillators, neurostimulators and the like.

DETAILED DESCRIPTION OF SPECIFIC EMBODIMENTS OF THE INVENTION

Figure 1:
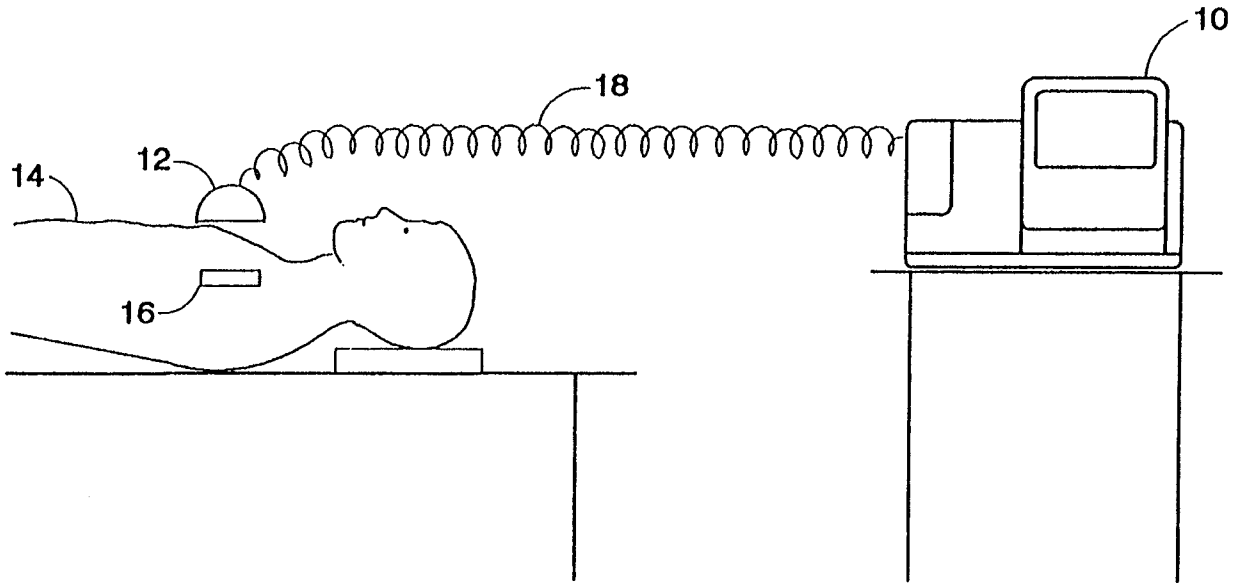
FIG. 1 shows a block diagram of one embodiment of the apparatus of the invention.

The present invention will now be more fully described with reference to the various figures of the drawings. FIG. 1 shows generally how a programmer can, in accordance with the present invention, be used in conjunction with the patient 14. A pacemaker 16 implanted in the patient 14 as is known in the art. Programming head 12 is connected via coiled cable 18 to programmer 10. It should also be understood that the present invention may be utilized in conjunction with other implantable medical devices, such as cardioverters, defibrillators, neurostimulators, cardiac assist systems, and the like.

Figure 2:
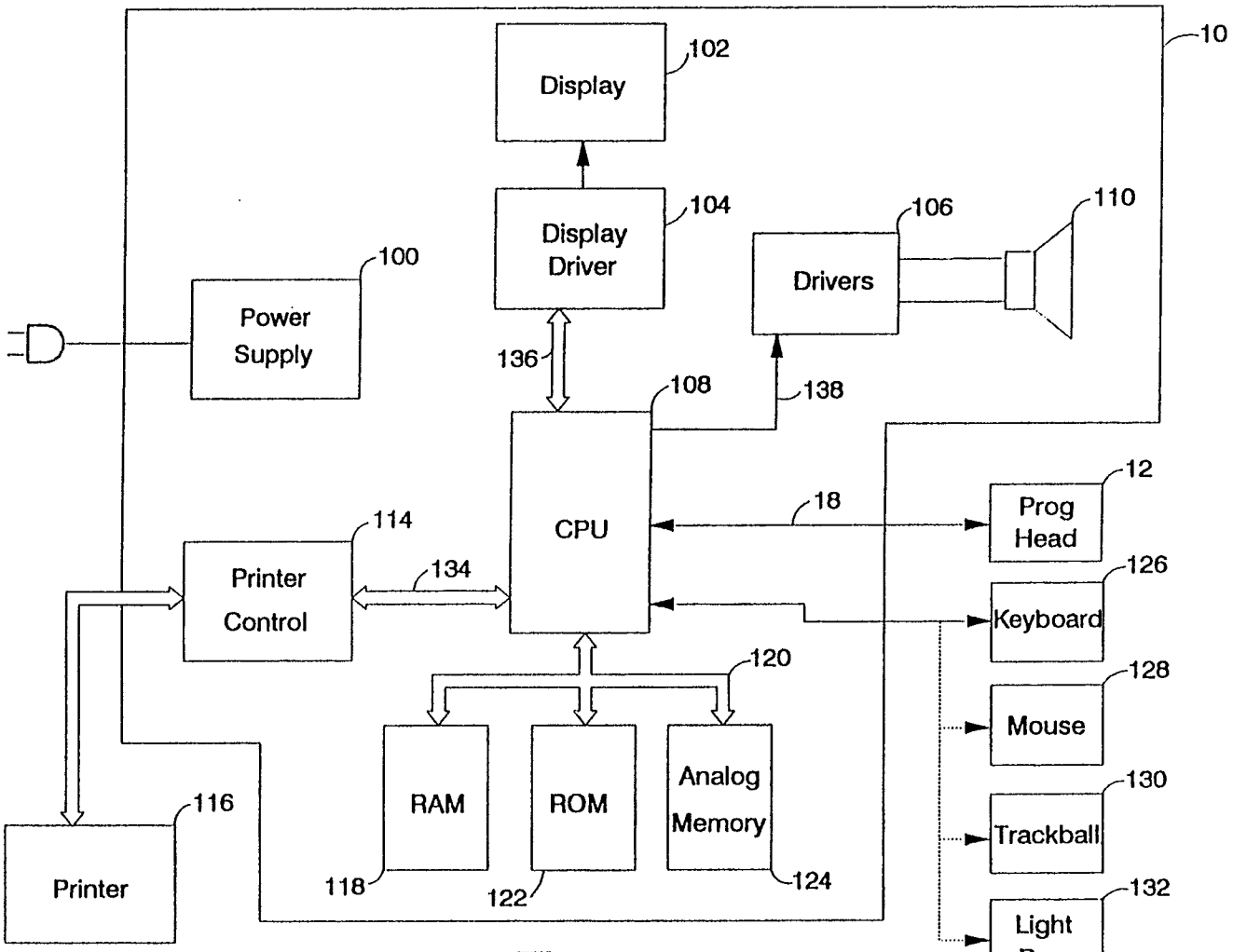
FIG. 2 shows a further detailed block diagram of an embodiment of the invention.

Turning to FIG. 2, a block diagram of programmer 10 from FIG. 1 is shown. Although the present invention is described in conjunction with FIG. 2 having a microprocessor based architecture, it will be understood that it could be implemented in logic-based, custom integrated circuit architecture or any other method of implementation, if desired. In the embodiment shown in FIG. 2, programmer 10 is connected to display device 102 which may be a cathode ray tube (CRT) display or liquid crystal display (LCD). In addition, programmer head 12, containing transmitting and receiving circuitry, is connected to the programmer 10 via stretchable cable 18. Data entry devices, such as keyboard 126, mouse 128, track ball 130, or light pen 132 may be manipulated by an operator for the entering of patient implant data and to control device function and operation. A printer 116 is typically used for hard copy printout of patient implant or follow-up data, including programmable parameter values, device and patient status and diagnostic data.

Microprocessor 108 in conjunction with RAM 118, ROM 122, and analog memory 124 are used to control the function of the device via stored executable programs. RAM 118, ROM 122, and analog memory 124 are connected to the microprocessor 108 via data bus 120. Printer 116 is connected to and controlled via the printer control circuitry 114 which is in turn connected to the microprocessor 108 via data bus 134. Display 102, used for displaying device function/status and to show diagnostic data, is connected to a display driver 104 which is in turn connected to the microprocessor 108 via data bus 136. Speaker 110, used to announce or speak words or phrases, is driven by annunciator driver 106 which is connected to, and controlled by, the microprocessor 108 via data bus 138. Power supply 100 powers the programmer 10 in accordance with common practice in the art. Not shown, but an option, would be to replace the power supply with rechargeable or primary cell batteries.

Analog memory 124 may be of the type incorporated in ISD 1016, a telecomunication monolithic integrated circuit from Information Storage Devices, Inc. Recorded voice data, or words, are stored in individual electrically alterable read only memory (EEROM) locations in analog memory 124. Analog memory 124 contains amplifier and filter functions to amplify and bandpass filter analog signals retrieved from memory. Additionally, analog memory 124 contains amplifier, bandpass, automatic gain control and sample and hold functions to enable programming or storing of the recorded voice data. The voice stored may be of any language to allow local language devices to be utilized, such as French, German, Italian, Spanish or English. This word list, or dictionary, may be loaded and stored into programmer 10 analog memory 124 during manufacture and updated periodically via replaceable cartridges or via loading software via diskettes, as is known in the art.

Figure 3:
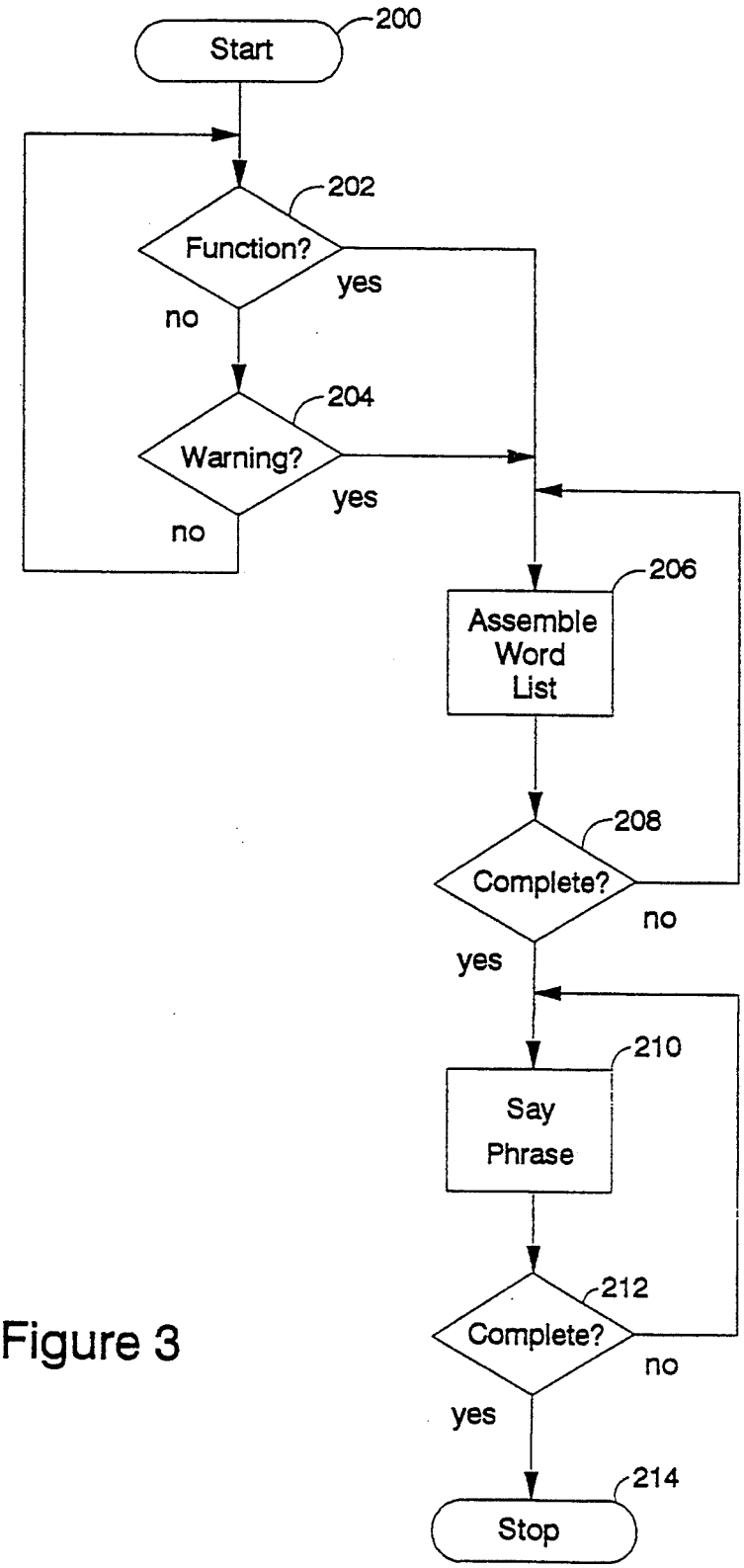
FIG. 3 shows a flow diagram of one embodiment of the invention.

Turning now to FIG. 3, a flow diagram is shown which illustrates the process in accordance with the presently disclosed embodiment of the invention. The flow diagram of FIG. 3 begins with a starting of the operation of the programmer of block 200 by detection of data entry from keyboard 126 (or alternatively, mouse 128, track ball 130, or light pen 132) or programmer function or status change. At block 202 the data entry is monitored for programmer function request. At block 204 the flow diagram monitors for a warning or a telemetry response indication requested by microprocessor 108. If neither of these items are identified the flow diagram returns to start block 200. If either of these items are valid, the microprocessor 108 in conjunction with the ROM 122 and analog memory 124 assembles a word list at 206. When the list is complete at block 208 the phrase or sentence is delivered to annunciator driver 106. Annunciator driver 106 drives the annunciator 110 or speaker. At block 212 the last word in the phrase is tested for, if yes, the flow diagram stops at block 214. If no, it returns to block 210 to continue reading the phrase.

Alternatively, a pacing systems analyzer may use the same analog memory 124 under control of microprocessor 108 to announce pacing amplitude or pulse width changes during threshold measurements on a beat-by-beat basis. Additionally, during intrinsic sensing measurements, the analyzer may announce R- or P-wave amplitudes on a beat-by-beat basis. Lastly, sensor signal characteristic amplitudes, widths or counts may be announced.

From the foregoing detailed descriptions of the particular embodiments of the invention, it should be apparent that a programmer has been disclosed which is provided with the capability of audio communication of data to facilitate the implant and follow-up process. While the particular embodiments of the present invention have been described herein detailed, it is to be understood that various alterations, modifications, and substitutions can be made therein without departing from the spirit and scope of the present invention, as described in the claims, which follow.

We claim:

1. In an apparatus for programming implantable medical devices, said programming apparatus having a data entry means for receiving and entering by operator manipulations, manifestations controlling operation of said medical device;

(a) having a transmitter means responsive to said manifestations entered via said data entry means for encoding and transmitting corresponding signals to said medical device;

(b) having means for receiving said encoded and transmitted status and diagnostic values from said medical device;

(c) having a display means for displaying a representation of said status and said diagnostic values;

(d) having a programmable microprocessor having a memory with a plurality of executable programs stored therein, said microprocessor comprising means responsive to said manifestations from said data entry means for providing corresponding signals to said transmitter means and means for activating said transmitter means to transmit the corresponding signals to said medical device whereby characteristics of said medical device may be selectively changed, said microprocessor comprising means responsive to said status and diagnostic values from said receiving means for causing said values to be displayed on said display means; the improvement comprising:

(i) audio means under control of said microprocessor for reproducing acoustic signals representing said status and said diagnostic values.

2. An apparatus recited in claim 1 wherein said reproduced acoustic signals are comprised of stored voice signals.

3. An apparatus recited in claim 2, further comprising means for defining a voltage level indicative of said stored voice signals;

(a) memory means for storing said voltage level;

(b) means for durable maintaining said voltage level; and (c) means for retrieving said voltage level.

4. An apparatus recited in claim 3, wherein said voltage level comprises an analog voltage level.

5. An apparatus recited in claim 3, wherein said memory means comprises electrically alterable read only memory.

6. In an implantable medical device system analyzer for verifying operation of a cardiac pacing system including a pacing lead and a cardiac pacemaker to be implanted, said analyzer having a data entry means for receiving and entering by operator manipulations, manifestations controlling operation of said analyzer; having a display means for displaying a representation of said operation of said medical device system; having a pacing means for stimulating said pacing lead; having a sensing means for sensing intrinsic heart signals conducted on said pacing lead; and having means for programming microprocessor having a memory with a plurality of executable programs stored therein, said microprocessor responsive to said manifestations from said data entry means and responsive to said sensing means and for activating said pacing means whereby characteristics of said cardiac pacing system may be evaluated and displayed on said display means; the improvement comprising:

(a) audio means under control of said microprocessor for reproducing acoustic signals representing said characteristic of said cardiac pacing system.

7. An apparatus recited in claim 6 wherein said reproduced acoustic signals are comprised of stored voice signals.

8. An apparatus recited in claim 7, further comprising means for defining a voltage level indicative of said stored voice signals;

(a) memory means for storing said voltage level;

(b) means for durable maintaining said voltage level; and (c) means for retrieving said voltage level.

9. An apparatus recited in claim 8, wherein said voltage level comprises an analog voltage level.

10. An apparatus recited in claim 8, wherein said memory means comprises electrically alterable read only memory.

11. A method of operating a programmer to be use in conjunction with an implantable medical device, said programmer being controlled by an operator and having capabilities of programming said medical device, receiving data representing status of said medical device and receiving telemetry representing diagnostic data from said medical device, said programmer generating acoustic signals representative or said status of said diagnostic data, said method comprising:

(a) storing programmer memory signals indicative of said medical device status, said programmer status and said diagnostic data;

(b) transmitting encoded signals to said medical device;

(c) receiving encoded signals from said medical device upon the request of said programmer via said encoded transmitted signals;

(d) assembling signals from said programmer memory; and (e) reproducing an audible manifestation of said assembled signals.

12. The method of claim 11 wherein the step of transmitting encoded signals to said medical device comprises transmitting signals for modifying a function of said medical device.

13. The method of claim 11 wherein the step of transmitting encoded signals to said medical device comprises transmitting signals for requesting said telemetry data.

14. The method of claim 11 wherein the step of assembling signals is comprised of assembling signals indicative of said status.

15. The method of claim 11 wherein the step of assembling signals is comprised of assembling signals indicative of said diagnostic data.

16. The method of claim 11 wherein the step of reproducing an audible manifestation of said assembled signals is comprised of reproducing an audible manifestation indicative of said status.

17. The method of claim 11 wherein the step of reproducing an audible manifestation of said assembled signals is comprised of reproducing an audible manifestation indicative of said diagnostic data.

18. A method of operating an analyzer to be used in conjunction with a medical device implanted within a patient, said analyzer being controlled by an operator and having capabilities of testing and measuring status of said medical device and simulation and sensing requirements of said medical device in said patient, said analyzer also generating acoustic signals representative of said status or said measured data, said method comprising:

(a) storing in analyzer memory signals indicative of said medical device status, said analyzer status and said measured data;

(b) assembling signals indicative of said status or said measured data from said analyzer memory; and (c) reproducing an audible representation of said assembled signals indicative of said status or said measured data.

19. The method of claim 18 wherein the step of assembling signals from said analyzer memory is comprised of assembling signals indicative of said status.

20. The method of claim 18 wherein the step of assembling signals from said analyzer memory is comprised of assembling signals indicative of said measured data.

21. The method of claim 18 wherein the step of reproducing an audible representation of said assembled signals is comprised of reproducing an audible representation of assembled signals indicative of said status.

22. The method of claim 18 wherein the step of reproducing an audible representation of said assembled signals is comprised of reproducing an audible representation of assembled signals indicative of said measured data.

* * * * *